United States Patent [19]

Chu

[11] Patent Number: 4,994,599

[45] Date of Patent: Feb. 19, 1991

[54] INTERMEDIATES FOR PRODUCING QUINOLONE-3-CARBOXYLIC ACIDS

[75] Inventor: Daniel T. Chu, Vernon Hills, Ill.

[73] Assignee: Abbott Laboratories, Abbott Park, Ill.

[21] Appl. No.: 397,366

[22] Filed: Aug. 21, 1989

Related U.S. Application Data

[63] Continuation of Ser. No. 123,097, Nov. 20, 1987, abandoned, which is a continuation of Ser. No. 797,057, Nov. 12, 1985, abandoned, which is a continuation of Ser. No. 514,715, Jul. 18, 1983, abandoned.

[51] Int. Cl.$^5$ ............................................ C07C 229/00
[52] U.S. Cl. ........................................ 560/43; 560/9; 558/44; 558/58
[58] Field of Search .................. 560/9, 43; 558/44, 58

[56] References Cited

U.S. PATENT DOCUMENTS 4,284,629 8/1981 Grohe et al. ........................ 514/212

Primary Examiner—Bruce Gray
Attorney, Agent, or Firm—Steven R. Crowley; Steven W. Weinstock

[57] ABSTRACT

A process for producing a 1,4-dihydro-4-oxo-quinoline-3-carboxylic acid by reacting an acctophenone with a dialkoxycarbonate to obtain the corresponding β-ketoester, treating the β-ketoester with a trialkylorthoformate in the presence of an acid anhydride followed by treatment with a substituted or unsubstituted amine to obtain the corresponding enaminoketoester, and then reacting the enaminoketoester with a strong base to obtain the corresponding quinoline-3-carboxylic acid ester. The acid ester may then be hydrolyzed, if desired, to obtain the quinoline-3-carboxylic acid. Also disclosed herein are compounds useful as intermediates useful in the production of quinoline-3-carboxylic acid.

8 Claims, No Drawings

INTERMEDIATES FOR PRODUCING QUINOLONE-3-CARBOXYLIC ACIDS

This application is a continuation of application Ser. No. 123,097, filed Nov. 20, 1987, which is a continuation of 06/797,057, filed 11/12/85, which is a continuation of 06/574,715, filed 07/18/83, now abandoned.

BACKGROUND AND SUMMARY

This invention relates to methods of producing quinoline derivatives and to compounds useful as intermediates in the production of 1,4-dihydro-4-oxo-quinoline-3-carboxylic acids.

It is known that certain 1,4-dihydro-4-oxo-quinoline-3-carboxylic acids exhibit antibacterial properties. For example, U.S. Pat. No. 4,017,622 discloses certain 7-piperazinyl-4-oxo-1,4-dihydroquinoline-3-carboxylic acid derivatives wherein the 1-position substituent is alkyl, benzyl or acetyl. U.S. Pat. No. 4,292,317 discloses certain 7-piperazinyl-6-halo-4-oxo-1,4-dihydroquinoline-3-carboxylic acid derivatives wherein the 1-position substituent is methyl, ethyl, vinyl or alkyl. In U.S. Pat. No. 4,284,629, various 4-oxo-1,4-dihydroquinoline-3-carboxylic acids are disclosed in which the 1-position substituent may be cycloalkyl, although corresponding derivatives containing a 7-piperazinyl substituent are not disclosed. The preparation of 1-ethyl-1,4-dihydro-4-oxo-quinoline-3-carboxylic acid ethyl ester by reacting N-ethylaniline with ethoxymethylene-malonic acid diethyl ester followed by cyclization of the product in the presence of polyphosphoric acid ester at elevated temperature is described in *J. Het. Chem.* 12, 557 (1975).

It has now been discovered that 1,4-dihydro-4-oxo-quinoline-3-carboxylic acids can be produced by reacting an acetophenone with a dialkoxycarbonate to obtain the corresponding β-ketoester, treating the β-ketoester with a trialkylorthoformate in the presence of an acid anhydride followed by treatment with a substituted or unsubstituted amine to obtain the corresponding enaminoketoester, and reacting the enaminoketoester with a strong base to obtain the corresponding 1,4-dihydro-4-oxo-quinoline-3-carboxylic acid ester.

DETAILED DESCRIPTION OF THE INVENTION

Compounds which can be produced by the process of the invention can be represented by the following formula I:

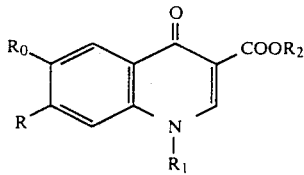

wherein $R_0$ is hydrogen, halo, nitro or loweralkoxy; R is hydrogen, halo, substituted or unsubstituted loweralkyl, substituted or unsubstituted loweralkoxy, alkylmercapto, cycloalkyl, phenyl, pyridinyl, substituted or unsubstituted pyrrolidinyl, piperazinyl or piperazinyl substituted by loweralkyl; $R_1$ is loweralkyl, loweralkoxy, pyridinyl, phenyl or substituted phenyl of the formula:

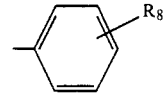

wherein $R_8$ is one or more radicals selected from hydrogen, halo, substituted or unsubstituted loweralkyl of 1 to 4 carbon atoms, hydroxy, substituted or unsubstituted loweralkoxy of 1 to 4 carbon atoms, nitro, substituted or unsubstituted amino, carboxyl or cyano; or $R_0$ and R can be taken together to form methylenedioxy, or can be taken together with the connecting carbon atoms of the aromatic ring to form furo or dihydrofuro; and $R_2$ is hydrogen, loweralkyl of 1 to 4 carbon atoms or pivaloyloxymethyl; and the pharmaceutically acceptable salts thereof; which are useful as antibacterial agents.

As used herein, the term "alkyl" refers to straight, branched and cyclic alkyl radicals having from 1 to 10 carbon atoms.

As used herein, the term "loweralkyl" means an alkyl radical having from 1 to 4 carbon atoms, i.e., methyl, ethyl, propyl or butyl. The presently most preferred alkyl radicals for use in connection with the present invention are methyl or ethyl. The term "substituted loweralkyl" means a loweralkyl group which is substituted with one or more radicals selected from hydroxy, halo and amino.

As used herein, the term "loweralkoxy" means a radical of the formula —$OR_3$, wherein $R_3$ is loweralkyl, as defined above. The term "substituted loweralkoxy" means a loweralkoxy group which is substituted with one or more radicals selected from hydroxy, halo and amino.

As used herein, the term "substituted amino" means a group of the formula

wherein $R_4$ and $R_5$ are independently selected from hydrogen and loweralkyl, with the proviso that at least one of $R_4$ and $R_5$ must be other than hydrogen.

As used herein, the term "leaving group" means a group capable of being displaced from the phenyl or quinoline moieties, and being replaced by the radical R in the case of $R_9$, as hereinafter defined, or to form a bond with the quinoline nitrogen in the case of RIO as hereinafter defined. Suitable leaving groups include halo, alkoxy, -S-alkyl, -O-tosyl, or -O-mesyl. Preferred leaving groups are halo, most preferably chloro.

As used herein, the term "halo" means chloro, fluoro, iodo and bromo, preferably chloro or fluoro.

As used herein, the term "pharmaceutically acceptable salts" means the nontoxic acid addition or alkaline earth metal salts of the compounds of Formula I. These salts can be prepared in situ during the final isolation and purification of the compounds of formula I, or by separately reacting the free base or acid functions with a suitable organic or inorganic acid or base, respectively. Representative acid addition salts include the hydrochloride, hydrobromide, sulfate, bisulfate, acetate, oxalate, valerate, oleate, palmitate, stearate, laurate, borate, benzoate, lactate, phosphate, tosylate, mesylate, citrate, maleate, fumarate, succinate, tartrate, napsylate, glucoheptonate, lactobionate, lauryl sulfate salts and the like. Representative alkal metal or alkaline earth metal salts include the sodium, calcium, potassium, and magnesium salts, and the like.

The present invention additionally relates, in part, to novel compounds of the formulae:

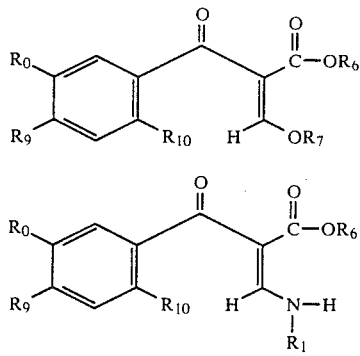

wherein $R_0$ and $R_1$ are as defined above in connection with formula I, $R_6$ and $R_7$ independently are alkyl, preferably loweralkyl, phenyl or benzyl, $R_9$ is hydrogen, loweralkyl, pyridinyl or a leaving group as defined above, or $R_0$ and $R_9$ can be taken together to form methylenedioxy, or can be taken together with the connecting atoms of the aromatic ring to form furo or dihydrofuro, and $R_{10}$ is a leaving group as defined above, which are useful as intermediates in the production of the compounds of formula I. Preferred compounds of formulas II and III are those compounds in which $R_9$ and $R_{10}$ are a leaving group, most preferably chloro. As shown in formulae II and III, and elsewhere herein, the $-OR_7$ group and the $-N-R_1$ group are shown in the transposition for purposes of illustration only, it being understood that these groups may be in the cis-position or the intermediates of formulae II and III may comprise a mixture of the trans- and cis-forms.

The compounds of formula I may be prepared in accordance with the following reaction scheme, in which the variable substituents are as defined above in connection with formulae I, II and III:

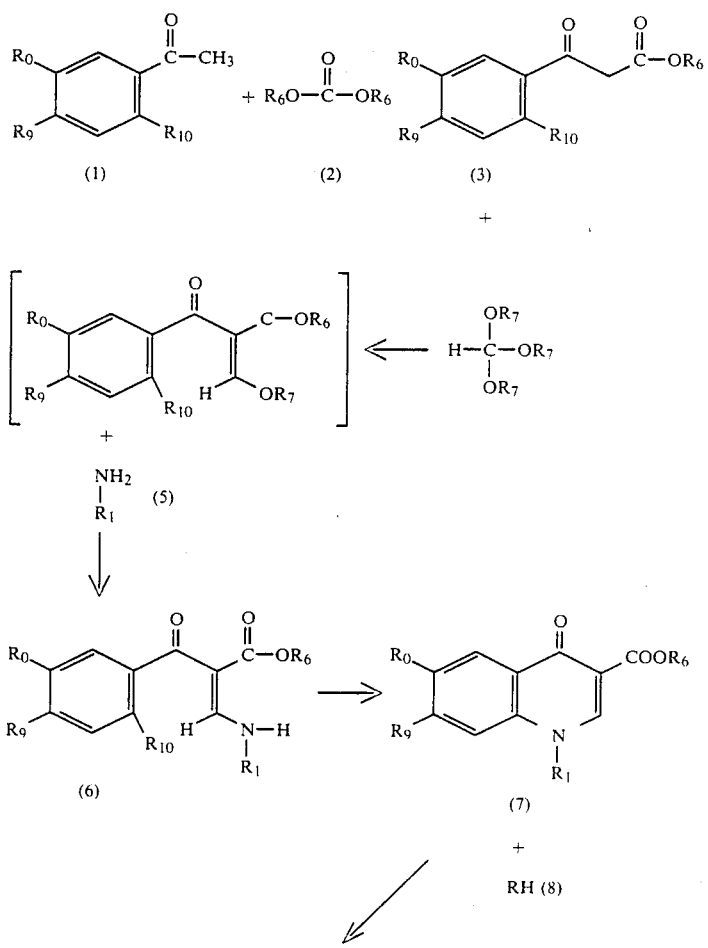

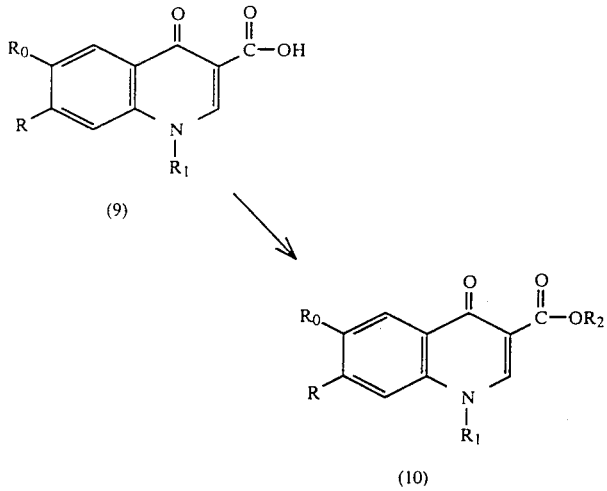

In accordance with the foregoing reaction scheme, the acetophenone (1) is reacted with a dialkoxycarbonate (2) in the presence of a strong base to obtain the corresponding β-ketoester (3). In the dialkoxycarbonate (2), $R_6$ may be an alkyl group of, for example, 1 to 10 carbon atoms, but is preferably loweralkyl, such as ethyl. Suitable bases include the metal hydrides, such as sodium hydride, potassium hydride and the like, as well as metal alkoxides in alcohol, such as sodium ethoxide in ethanol. The presently preferred base for this purpose is sodium hydride. Formation of the β-ketoester (3) is facilitated by reacting the acetophenone (1) with the dialkoxycarbonate (2) at elevated temperatures, such as from about 20° C. to about 120° C., and preferably from about 30° C. to about 90° C. until completion of the reaction. The β-ketoester may then be separated from the reaction mixture in a conventional manner.

The β-ketoester (3) is then treated with a trialkylorthoformate (4) in the presence of an acid anhydride, preferably acetic anhydride, followed by reacton with substituted or unsubstituted amine (5) to obtain the enaminoketoester (6). In the trialkylorthoformate (4), $R_7$ may be an alkyl group of, for example, from 1 to 10 carbon atoms, but is preferably loweralkyl, such as ethyl. Reaction with the trialkylorthoformate is preferably conducted at elevated temperatures, such as from about 50° C. to about 150° C., preferably from about 100° C. to about 140° C., to obtain an oily liquid, which may be isolated or unisolated, as desired (shown in brackets in the reaction scheme). Reaction of the latter with the substituted or unsubstituted amine (5) is preferably conducted in an appropriate aprotic or non-aprotic solvent, preferably methylene chloride or tetrahydrofuran, and may be conducted at room or suitable elevated temperature, as desired.

The enaminoketoester (6) is then cyclized, such as by treatment with a strong base as defined above, preferably sodium hydride, to obtain the 1,4-dihydro-4-oxo-quinoline-3-carboxylic acid ester (7). Cyclization is conducted in the presence of an aprotic solvent, such as dimethoxyethane, dimethylformamide, tetrahydrofuran or chlorobenzene, and is preferably conducted at temperatures of about 20° C. to about 145° C., more preferably at the reflux temperature of the solvent employed.

The ester (7) is subjected to hydrolysis, such as by treatment with sodium hydroxide, to form the free acid, followed by displacement of $R_9$ with R-H (8) by techniques known in the art to obtain the desired 1,4-dihydroxy-4-oxo-quinoline-3-carboxylic acid (9).

The 1,4-dihydro-4-oxo-quinoline-3-carboxylic acid (9) can then be converted into the corresponding ester (10), if desired, by conventional esterification procedures, such as by treating the free acid (9) with the appropriate alcohol in the presence of an acid catalyst, by converting the free acid (9) into the corresponding acid chloride followed by displacement of the chloro radical with the appropriate alcohol, or by treating the sodium salt of the acid (9) with a suitable reactive halide, such as chloro-methylpivalate in dimethoxyethane to obtain, for example, the pivaloyloxymethyl ester (10) wherein $R_2$ is —$CH_2OCOC(CH_3)_3$.

The foregoing may be better understood from the following examples, which are presented for purposes of illustration and are not intended to limit the scope of the inventive concepts. As used in the following examples, the references to compounds, such as (1), (2), (3), etc., and to substituents, such as R, $R_1$, $R_2$, etc., refer to the corresponding compounds and substituents in the foregoing reaction scheme and in formulae I, II and III.

EXAMPLE 1

1-Phenyl-6-fluoro-1,4-dihydro-4-oxo-7-(1-piperazinyl)-quinoline-3-carboxylic acid (a) To a cold solution of 20.5 g. 2,4-dichloro-5-fluoroacetophenone in 300 ml. diethylcarbonate is slowly added of 8.2 g. 60% sodium hydride-in-oil suspension. The mixture is heated at 80° C. for 1½ hours, then poured into 700 ml. ice cold water solution containing 25 ml. acetic acid. The mixture is extracted with three 400 ml. portions of ether. The organic phase is dried over $MgSO_4$, evaporated and the obtained liquid is distilled at 111° C. at 0.7 mm of Hg pressure to give 22.2 g. of (3), wherein $R_6=C_2H_5$, $R_0=F$, $R_9=R_{10}=Cl$.

(b) A solution of 15.18 g. of β-keto ester (3) ($R_6=C_2H_5$, $R_0=F$, $R_9=R_{10}=Cl$) in 14 ml. of triethylorthoformate and 35 ml. of acetic anhydride is heated at 135° C. for 1½ hours with the removal of the ethyl acetate formed during the reaction. The solution is evaporated under reduced pressure to a mobile oil. The oil is then dissolved in 150 ml. of methylene chloride and 7.5 ml. of aniline is added into the solution. After 1 hour, the solution is evaporated to dryness and crystallized from 200 ml. of hexane and 5 ml. of ether yielding (6), wherein $R_6 = C_2H_5$, $R_1$ = phenyl, $R_0$ = F, $R_9 = R_{10} = Cl$, in 89% yield, m.p. 96°-97° C.

(c) To a cold solution of 13.9 g. of the preceding product (6), ($R_6 = C_2H_5$, $R_1$ = H, $R_0$ = F, $R_9 = R_{10}$ = Cl) in 140 ml. dimethoxymethane (DME) is slowly added 1.49 g. of a 60% sodium hydride-in-oil suspension. The mixture is refluxed for 4½ hours and is cooled and diluted with water to a volume of 1.5 liters. The mixture is then filtered and the solid is washed with a 1:1 hexane/ether solution to obtain 10.4 g. of (7) wherein $R_6 = C_2H_5$ and $R_1$ = phenyl, $R_9$ = F, $R_9$ = Cl in 81% yield.

(d) To a suspension of 5.4 g. of (7) ($R_6 = C_2H_5$, $R_1$ = phenyl, $R_0$ = F, $R_9$ = Cl) in 30 ml. THF is added a sodium hydroxide solution (0.73 g. in 20 ml. $H_2O$). The mixture is heated at 80° C. for 1 hour resulting in a clear solution which is evaporated under reduced pressure to dryness. The solid is dissolved in 200 ml. $H_2O$, and 2 ml. acetic acid is added. The resulting precipitate is filtered and washed with cold water, crystallized from dimethylformamide (DMF) to produce 4.6 g. of 7-chloro-1-phenyl-6-fluoro-1,4-dihydro-4-oxoquinoline-3-carboxylic acid (7) ($R_6$ = hydrogen, $R_1$ = phenyl, $R_0$ = F, $R_9$ = Cl), m.p. 271°-273° C.

(e) To a solution of 1.25 g. of 7-chloro-1-phenyl-6-fluoro-1,4-dihydro-4-oxo-quinoline-3-carboxyli c acid in 15 ml. of 1-methyl-2-pyrrolidinone at 115° C. is added 2 ml. piperazine. After stirring at 100° C. for 20 hours, the solvent is removed by reduced pressure to dryness. Ethanol is added to the residue and the resulting mixture is filtered and washed with ether and then washed with very small amounts of cold water. The resulting dried solid is suspended in 30 ml. $H_2O$ and 2.35 ml. 1N HCl is added to and warmed to dissolve. Removal of the solvent under reduced pressure gives 835 mg. hydrochloride salt of 1-phenyl-6-fluoro-1,4-dihydro-4-oxo-7-(1-piperazinyl) quinoline-3-carboxylic acid (9) ($R_0$ = F, $R_1$ = phenyl, R = 1-piperazinyl).

To the hydrochloride salt is added one molar equivalent of an aqueous solution of sodium hydroxide, and the resulting precipitate is filtered to obtain 1-phenyl-6-fluoro-1,4-dihydro-4-oxo-7-(1-piperazinyl)-q inoline-3-carboxylic acid.

EXAMPLE 2

1-Phenyl-6-fluoro-1,4-dihydro-4-oxo-7-(1-(4-methyl)-piperazinyl)quinoline-3-carboxylic acid The procedure of Example 1 is repeated replacing piperazine in Example 1(e) with N-methylpiperazine to obtain 1-phenyl-6-fluoro-1,4-dihydro-4-oxo-7-(1-(4-methyl)-piperazinyl)quinoline-3-carboxylic acid (9) ($R_0$ = F, $R_1$ = phenyl, R = 1-(4-methyl)piperazinyl) and its hydrochloride salt.

EXAMPLE 3

1-Phenyl-6-fluoro-1,4-dihydro-4-oxo-7-(1(4-ethyl)-piperazinyl)-quinoline-3-carboxylic acid The procedure of Example 1 is repeated replacing replacing piperazine in Example 1(e) with N-ethylpiperazine to obtain the 1-phenyl-6-fluoro-1,4-dihydro-4-oxo-7-(1-(4-ethyl)-piperazinyl) quinoline-3-carboxylic acid (9) ($R_0$ = F, $R_1$ = phenyl, R = 1-(4-ethyl)-piperazinyl) and its hydrochloride salt.

EXAMPLE 4

1-p-Fluorophenyl-6-fluoro-1,4-dihydro-4-oxo-7-(1-piperazine)quinoline-3-carboxylic acid (a) In the described fashion as Example 1(b) replacing aniline with p-fluoroaniline, one obtains the anaminoketoester (6) ($R_6 = C_2H_5$, $R_0$ = F, $R_9 = R_{10}$ = Cl, $R_1$ = p-fluorophenyl) in 78% yield, m.p. 108° C.

(b) By following the Example 1(c) and 1(d), the preceding compound (6) ($R_6 = C_2H_5$, $R_0$ = F, $R_9 = R_{10}$ = Cl, $R_1$ = p-fluorophenyl) yields 7-chloro-1-p-fluorophenyl-6-fluoro-1,4-dihydro-4-oxo-quinoline-3-carboxylic acid (7) ($R_6$ = H, $R_0$ = F, $R_0$ = Cl, $R_1$ = p-fluorophenyl).

(c) In the described fashion as Example 1(e) the above acid (7) ($R_6$ = H, $R_0$ = F, $R_9$ = Cl, $R_1$ = p-fluorophenyl) gives the desired 1-p-fluoro-phenyl-6-fluoro-1,4-dihydro-4-oxo-7-(1-piperaziny l)-quinoline-3-carboxylic acid (9) ($R_1$ = p-fluorophenyl, $R_0$ = F, R = 1 = piperazinyl) and its hydrochloride salt.

EXAMPLE 5

1-p-Fluorophenyl-6-fluoro-1,4-dihydro-4-oxo-7(1-(4-methyl)-piperazinyl)-quinoline-3 -carboxylic acid In the described fashion as Example 1(e), replacing piperazine with N-methylpiperazine, the acid (7) ($R_6$ = H, $R_0$ = F, $R_9$ = Cl, $R_1$ = p-fluorophenyl) in Example 4(b) yields the described 1-p-fluorophenyl-6-fluoro-1,4-dihydro-4-oxo-7-(1-(4-methyl)-piperazinyl)-quinoline-3-carboxylic acid (9) ($R_0$ = F, $R_1$ = p-fluorophenyl, R = -(4-methyl)piperazinyl) and its hydrochloride salt.

EXAMPLE 6

1-p-chlorophenyl-6-fluoro-1,4-dihydro-4-oxo-(1-piperazinyl)quinoline-3-carboxylic acid (a) In the described fashion as Example 1(b) replacing aniline with p-chloroaniline, one obtains the enaminoketoester (6) ($R_6 = C_2H_5$, $R_0$ = F, $R_9 = R_{10}$ = Cl, $R_1$ = p-chlorophenyl) in 64% yield.

(b) By following Example 1(c) and 1(d), the preceding compound (6) ($R_6 = C_2H_5$, $R_0$ = F, $R_9 = R_{10}$ = Cl, $R_1$ = p-chlorophenyl) yields 7-chloro-1-p-chlorophenyl-6-fluoro-1,4-dihydro-4-oxo-quinoline-3-carboxylic acid (7 ($R_6$ = H, $R_0$ = F, $R_9$ = Cl, $R_1$ = p-chlorophenyl).

(c) In the described fashion as Example 1(e) the above acid (7) ($R_6$ = H, $R_0$ = F, $R_9$ = Cl, $R_1$ = p-chlorophenyl) gives the described 1-p-chlorophenyl-6-fluoro-1,4-dihydro-4-oxo-7-(piperazinyl) -quinoline-3-carboxylic acid (9) ($R_1$ = p-chlorophenyl, $R_0$ = F, R = 1-piperazinyl) and its hydrochloride salt.

EXAMPLE 7

1-p-Chlorophenyl-6-fluoro-1,4-dihydro-4-oxo-7-(1-(4-methyl)-piperazinyl)quinoline-3 -carboxylic acid In the described fashion as Example 1(e), replacing piperazine with N-methylpiperazine, the acid (7) ($R_6$ = H, $R_0$ = F, $R_9$ = Cl, $R_1$ = p-chlorophenyl) in Example 6(b) yields the desired 1-p-chlorophenyl-6-fluoro-1,4-dihydro-4-oxo-7-(1-(4-methyl)piperazinyl)-quinoline-3-carboxylic acid (9) ($R_1$ = p-chlorophenyl, $R_0$ = F, R = 1-(4-methyl)piperazinyl) and its hydrochloride salt.

EXAMPLE 8

1-p-Methoxyphenyl-6-fluoro-1,4-dihydro-4-oxo-(1-piperazinyl)quinoline-3-carboxylic acid (a) In the described fashion as Example 1(b) replacing aniline with p-methoxyaniline, one obtains the enaminoketoester (6 ($R_6=C_2H_5$, $R_0=F$, $R_9=R_{10}=Cl$, $R_1=$p-methoxyphenyl) in 77% yield (m.p. 105° C.)

(b) By following the Example 1(c) and 1(d), the preceding compound (6 ($R_6=C_2H_5$, $R_0=F$, $R_9=R_{10}=Cl$, $R_1=$p-methoxyphenyl) yields 7-chloro-1-p-methoxyphenyl-6-fluoro-1,4-dihydro-4-oxo-quinoline-3-carboxylic acid (7) ($R_6=H$, $R_0=F$, $R_9=Cl$, $R_1=$p-methoxyphenyl).

(c) In the described fashion as Example 1(e) the above acid (7) ($R_6=H$, $R_0=F$, $R_9=Cl$, $R_1=$p-methoxyphenyl) gives the desired 1-p-methoxy-phenyl-6-fluoro-1,4-dihydro-4-oxo-7-(1-piperarinyl)-quinoline-3-carboxylic acid (9) ($R_0=F$, $R=$1-piperazinyl, $R_1=$p-methoxyphenyl) and its hydrochloride salt.

EXAMPLE 9

1-p-Methoxyphenyl-6-fluoro-1,4-dihydro-4-oxo-7(1-(4-methyl)-piperazinyl) quinoline-3-carboxylic acid In the described fashion as Example 1(e), replacing piperazine with N-methylpiperazine, the acid (7) ($R_6=H$, $R_0=F$, $R_9=Cl$, $R_1=$p-methoxyphenyl) in Example 8(b) yields the described 1-p-methoxyphenyl-6-fluoro-1,4-dihydro-4-oxo-7-(1-(4-methyl)-piperazinyl) quinoline-3-carboxylic acid (9) ($R_0=F$, $R_1=$p-methoxyphenyl, $R=$1-(4-methyl)piperazinyl) and its hydrochloride salt.

EXAMPLE 10

1-p-Methylphenyl-6-fluoro-1,4-dihydro-4-oxo(1-piperazinyl)quinoline-3-carboxylic acid (a) In the described fashion as Example 1(b) replacing aniline with p-methylaniline, one obtains the enaminoketoester (6) ($R_6=C_2H_5$, $R_0=F$, $R_9=R_{10}=Cl$, $R_1=$p-methylphenyl) in 80% yield (m.p. 115.5° C.)

(b) By following the Example 1(c) and 1(d), the preceding compound (6) ($R_6=C_2H_5$, $R_0=F$, $R_9=R_{10}=Cl$, $R_1=$p-methylphenyl) yields 7-chloro-1-p-methylphenyl-6-fluoro-1,4-dihydro-4-oxo-quinoline-3-carboxylic acid (7) ($R_6=H$, $R_0=F$, $R_9=Cl$, Cl, $R=$p-methylphenyl).

(c) In the described fashion as Example 1(e) the above acid (7) ($R_6=H$, $R_0=F$, $R_9=Cl$, $R_1=$p-methylphenyl) gives the desired 1-p-methylphenyl-6-fluoro-1,4-dihydro-4-oxo-7(1-piperazinyl)quinoline-3-carboxylic acid (9) ($R_0=F$, $R_1=$p-methylphenyl, $R=$1-piperazinyl) and its hydrochloride salt.

EXAMPLE 11

1-p-Methylphenyl-6-fluoro-1,4-dihydro-4-oxo-7-(1(4-methyl)-piperazinyl)quinoline-3 -carboxylic acid In the described fashion as Example 1(e), replacing piperazine with N-methylpiperazine, the acid (7) ($R_6=H$, $R_0=F$, $R_9=Cl$, $R_1=$p-methylphenyl) in Example 10(b) yields the desired 1-p-methylphenyl-6-fluoro-1,4-dihydro-4-oxo-7-(1-(4-methyl)-piperazinyl) quinoline-3-carboxylic acid (9) ($R_0=F$, $R_1=$p-methylphenyl, $R=$1-(4-methyl)piperazinyl) and its hydrochloride salt.

EXAMPLE 12

1-p-Hydroxyphenyl-6-fluoro-1,4-dihydro-4-oxo-(1-piperazinyl)quinoline-3-carboxylic acid (a) In the described fashion as Example 1(b) replacing aniline with p-hydroxyaniline, one obtains the enaminoketoester (6) ($R_6=C_2H_5$, $R_0=F$, $R_9=R_{10}=Cl$, $R_1=$p-hydroxyphenyl) in 84.4% yield.

(b) By following the Example 1(c) and 1(d), the preceding compound (6) ($R_6=C_2H_5$, $R_0=F$, $R_9=R_{10}=Cl$, $R_1=$p-hydroxyphenyl) yields 7-chloro-1-p-hydroxyphenyl-6-fluoro-1,4-dihydro-4-oxo-quinoline-3-carboxylic acid (7 ($R_6=H$, $R_0=F$, $R_9=Cl$, $R_1=$p-hydroxyphenyl) in good yield.

(c) In the described fashion as Example 1(e) the above acid (7) ($R_6=H$, $R_0=F$, $R_9=Cl$, $R_1=$p-hydroxyphenyl) gives the desired 1-p-hydroxy-phenyl-6-fluoro-1,4-dihydro-4-oxo-7-(1-piperazinyl-quinoline-3-carboxylic acid (9) ($R_0=F$, $R_1=$p-hydroxyphenyl, $R=$1-piperazinyl) and its hydrochloride salt.

EXAMPLE 13

1-p-hydroxyphenyl-6-fluoro-1,4-dihydro-4-oxo-7(-(4-methyl)-piperazinyl)quinoline-3 -carboxylic acid In the described fashion as Example 1(e), replacing piperazine with N-methylpiperazine, the acid 7 ($R_6=H$, $R_0=F$, $R_9=Cl$, $R_1=$p-hydroxyphenyl) in Example 12(b) yields the desired 1-p-hydroxyphenyl-6-fluoro-1,4-dihydro-4-oxo-(1-(4-methyl)-piperazinyl)quinoline-3-carboxylic acid (9) ($R_0=F$, $R_1=$p-hydroxyphenyl, $R=$-(4-methyl)-piperazine) and its hydrochloride salt.

EXAMPLE 14

1-o-Fluorophenyl-6-fluoro-1,4-dihydro-4-oxo-(1-piperazinyl)quinoline-3-carboxylic acid (a) In the described fashion as Example 1(b) replacing aniline with o-fluoroaniline, one obtains the enaminoketoester (7)($R_6=C_2H_5$, $R_0=F$, $R_9=R_{10}=Cl$, $R_1=$o-fluorophenyl) in 78.8% yield (m.p. 90°-92° C.).

(b) By following the Example 1(c) and 1(d), the preceding compound (6) ($R_6=C_2H_5$, $R_0=F$, $R_9=R_{10}=Cl$, $R_1=$o-fluorophenyl) yields 7-chloro-1-o-fluorophenyl-6-fluoro-1,4-dihydro-4-oxo-quinoline-3-carboxylic acid (7) ($R_6=H$, $R_0=F$, $R_9=Cl$, $R_1=$o-fluorophenyl).

(c) In the described fashion as Example 1(e) the above acid (7) ($R_6=H$, $R_0=F$, $R_9=Cl$, $R_1=$o-fluorophenyl) gives the desired 1-o-fluoro-phenyl-6-fluoro-1,4-dihydro-4-oxo-7-(1-piperazinyl)-quinoline-3-carboxylic acid (9)($R_0=F$, $R_1=$o-fluorophenyl, $R=$1-piperazinyl) and its hydrochloride salt.

EXAMPLE 15

1-o-Fluorophenyl-6-fluoro-1,4-dihydro-4-oxo-7(1-(4-methyl)-piperazinyl)quinoline-3 carboxylic acid In the described fashion as Example 1(e), replacing piperazine with N-methylpiperazine, the acid (7) ($R_6=H$, $R_0=F$, $R_9=Cl$, $R_1=$o-fluorophenyl) in Example 14(b) yields the desired 1-o-fluorophenyl-6-fluoro-1,4-dihydro-4-oxo-(1-(4-methyl)-piperazinyl)quinoline-3-carboxylic acid (9) ($R_0=F$, $R_1=$o-fluorophenyl, $R=$1-(4-methyl)-piperazinyl) and its hydrochloride salt.

EXAMPLE 16

1-m-Fluorophenyl-6-fluoro-1,4-dihydro-4-oxo-(1-piperazinyl)quinoline-3-carboxylic acid (a) In the described fashion as Example 1(b), replacing aniline with m-fluoroaniline, one obtains the enaminoketoester (6) ($R_6=C_2H_5$, $R_0=F$, $R_9=R_{10}=Cl$, $R_1=$m-fluorophenyl)- in 68.5% yield (m.p. 104°-104° C.).

(b) By following the Example 1(c) and 1(d), the preceding compound (6) ($R_6=C_1H_5$, $R_1=$m-fluorophenyl, $R=F$, $R_9=R_{10}=Cl$) yields 7-chloro-1-m-fluorophenyl-6-fluoro-1,4-dihydro-4-oxo-quinoline-3-carboxylic acid (7) ($R_6=H$, $R_0=F$, $R_9=Cl$, $R_1=$m-fluorophenyl).

(c) In the described fashion as Example 1(e) the above acid (7) ($R_6=H$, $R_0=F$, $R_9=Cl$, $R_1=$m-fluorophenyl) gives the described 1-m-fluoro-phenyl-6-fluoro-1,4-dihydro-4-oxo-7-(1 -piperazinyl-quinoline-3-carboxylic acid (9)($R_0=F$, $R=1$-piperazinyl, $R_1=$m-fluorophenyl) and its hydrochloride salt.

EXAMPLE 17

1-p-Cyanophenyl-6-fluoro-1,4-dihydro-4-oxo-(1-piperazinyl)quinoline-3-carboxylic acid (a) In the described fashion as Example 1(b), replacing aniline with p-cyanoaniline, one obtains the enaminoketoester (6) ($R_6=C_2H_5$, $R_0=F$, $R_9=R_{10}=Cl$, $R_1=Cl$, $R_1=$p-cyanophenyl) in 91.2% yield.

(b) By following the Example 1(c) and 1(d), the preceding compound (6) ($R_6=C_2H_5$, $R_1=$p-cyanophenyl, $R_0=F$, $R_9=R_{10}=Cl$) yields 7-chloro-1-p-cyanophenyl-6-fluoro-1,4-dihydro-4-oxo-quinoline-3-carboxylic acid (7) ($R_6=H$, $R_0=F$, $R_9=Cl$, $R_1=$p-cyanophenyl).

(c) In the described fashion as Example 1(e) the above acid (7) ($R_6=H$, $R_0=F$, $R_9=Cl$, $R_1=$p-cyanophenyl) gives the desired 1-p-cyano-phenyl-6-fluoro-1,4-dihydro-4-oxo-7-(1 -piperazinyl)-quinoline-3-carboxylic acid (9) ($R_0=F$, $R=1$-piperazinyl, $R_1=$p-cyanophenyl) and its hydrochloride salt.

EXAMPLE 18

1-p-cyanophenyl-6-fluoro-1,4-dihydro-4-oxo-7-(1(4-methyl)-piperazinyl)quinoline-3 -carboxylic acid In the described fashion as Example 1(e), replacing piperazine with N-methylpiperazine, the acid (7) ($R_6=H$, $R_0=F$, $R_9=Cl$, $R_1=$p-cyano-phenyl) in Example 18(b) yields the described 1-p-cyanophenyl-6-fluoro-1,4-dihydro-4-oxo-7-(1-(4-methyl)-piperazinyl)-quinoline-3-carboxylic acid (9) ($R_0=F$, $R_1=$p-cyanophenyl, $R=1$-(4-methyl)-piperazinyl) and its hydrochloride salt.

EXAMPLE 19

1-4-pyridyl-6-fluoro-1,4-dihydro-4-oxo-(1-piperazinyl)-quinoline-3-carboxylic acid (a) In the described fashion as Example 1(b), replacing aniline with 4-aminopyridine, one obtains the enaminoketoester (6) ($R_6=C_2H_5$, $R_0=F$, $R_9=Cl$, $R_1=$4-pyridyl) in 70% yield as an oil.

(b) By following the Example 1(c) and 1(d), the preceding compound (6) ($R_6=C_2H_5$, $R_0=F$, $R_9=R_{10}=Cl$, $R_1=$4-pyridyl) yields 7-chloro-1-4-pyridyl-6-fluoro-1,4-dihydro-4-oxo-quinoline-3-carboxylic acid (7) ($R=H$, $R_0=F$, $R_9=Cl$, $R_1=$4-pyridyl).

(c) In the described fashion as Example 1(e), the above acid (7) ($R_6=H$, $R_0=F$, $R_9=Cl$, $R_1=$4-pyridyl) gives the desired 1-4-pyridyl-6-fluoro-1,4-dihydro-4-oxo-7-(1 -piperazinyl)quinoline-3-carboxylic acid (9) ($R_0=F$, $R=1$-piperazinyl, $R_1=$4-pyridyl) and its hydrochloride salt.

EXAMPLE 20

1-4-Pyridyl-6-fluoro-1,4-dihydro-4-oxo-7-(1(4-methyl)-piperazinyl)quinoline-3 carboxylic acid In the described fashion as Example 1(e), replacing piperazine with N-methylpiperazine, the acid (7) ($R_6=H$, $R_0=F$, $R_9=Cl$, $R_1=$4-pyridyl) in Example 19(b) yields the desired 1-4-pyridyl-6-fluoro-1,4-dihydro-4-oxo-7-(1-(4-methyl )-piperazinyl)-quinoline-3-carboxylic acid (9) ($R_0=F$, $R_1=$4-pyridyl, $R=1$-(4-methyl)-piperazinyl).

EXAMPLE 21

1-3-pyridyl-6-fluoro-1,4-dihydro-4-oxo-(1-piperazinyl)-quinoline-3-carboxylic acid (a) In the described fashion as Example 1(b) replacing aniline with 3-aminopyridine, one obtains the enaminoketoester (6) ($R_6=C_2H_5$, $R_0=F$, $R_9=R_{10}=Cl$, $R_1=$3-pyridyl) in 80% yield.

(b) By following the Example 1(c) and 1(d), the preceding compound (6) ($R_6=C_2H_5$, $R_0=F$, $R_9=R_{10}=Cl$, $R_1=$3-pyridyl) yields 7-chloro-3-pyridyl-6-fluoro-1,4-dihydro -4-oxo-quinoline-3-carboxylic acid (7) ($R_6=H$, $R_0=F$, $R_9=Cl$, $R_1=$3-pyridyl).

(c) In the described fashion as Example 1(e) the above acid (7) ($R_6=H$, $R_0=F$, $R_9=Cl$, $R_1=$3-pyridyl) gives the desired 1-3-pyridyl-6-fluoro-1,4-dihydro-4-oxo-7-(1 -piperazinyl)quinoline-3-carboxylic acid (9) ($R_0=F$, $R_1=$3-pyridyl, $R=1$-piperazinyl) and its hydrochloride salt.

EXAMPLE 22

1-3-pyridyl-6-fluoro-1,4-dihydro-4-oxo-7-(1(4-methyl)-piperazinyl)quinoline-3 carboxylic acid In the described fashion as Example 1(e), replacing piperazine with N-methylpiperazine, the acid (7) ($R_6=H$, $R_0=F$, $R_9=Cl$, $R_1=$3-pyridyl) in Example 21(b) yields the desired 1-3-pyridyl-6-fluoro-1,4-dihydro-4-oxo-7-(1-(4-methyl )-pipiperazinyl)-quinoline-3-carboxylic acid in good yield (9) ($R_0=F$, $R=1$-(4-methyl)-piperazinyl, $R_1=$3-pyridyl).

EXAMPLE 23

In similar fashion as Example 1, the use of various substituted amines and other amino aromatic compounds in place of aniline and the use of appropriate piperazine, the following additional compounds of formula I wherein $R_2$ is hydrogen, and Their hydrochloride salts, are made as summarized in Table I.

TABLE I

| Aniline Replacement | Piperazine Replacement | Compound Obtained | | |
|---|---|---|---|---|
| | | $R_0$ | R | $R_1$ |
| p-nitroaniline | N-methylpiperazine | F | 1-(4-methyl)piperazinyl | p-nitrophenyl |
| p-nitroaniline | piperazine | F | 1-piperazinyl | p-nitrophenyl |
| p-dimethylaminoaniline | piperazine | F | 1-piperazinyl | p-dimethylaminophenyl |

TABLE I-continued

| Aniline Replacement | Piperazine Replacement | Compound Obtained $R_0$ | R | $R_1$ |
|---|---|---|---|---|
| p-aminobenzoic acid | piperazine | F | 1-piperazinyl | p-carboxylphenyl |
| p-trifluoromethylaniline | piperazine | F | 1-piperazinyl | p-trifluoromethylphenyl |
| N-methoxyamine | piperazine | F | 1-piperazinyl | methoxy |
| N-methoxyamine | N-methylpiperazine | F | 1-(4-methyl)piperazinyl | methoxy |
| N-phenoxyamine | piperazine | F | 1-piperazinyl | phenoxy |
| N-p-hydroxyphenoxyamine | piperazine | F | 1-piperazinyl | p-hydroxyphenoxy |
| N-p-fluorophenoxyamine | piperazine | F | 1-piperazinyl | p-fluorophenoxy |
| ethylamine | piperazine | F | 1-piperazinyl | ethyl |
| ethylamine | N-methylpiperazine | F | 1-(4-methyl)piperazinyl | ethyl |
| cyclopropylamine | piperazine | F | 1-piperazinyl | cyclopropyl |
| cyclopropylamine | N-methylpiperazine | F | 1-(4-methyl)piperazinyl | cyclopropyl |
| 2-ethanolamine | piperazine | F | 1-piperazinyl | 2-hydroxyethyl |
| 1,2-diaminoethane | piperazine | F | 1-piperazinyl | 2-aminoethyl |
| N-methoxyamine | 3-amino-pyrrolidine | F | 1-(3-amino)pyrrolidinyl | methoxy |
| ethylamine | 3-amino-pyrrolidine | F | 1-(3-amino)pyrrolidinyl | ethyl |
| cyclopropylamine | 3-amino-pyrrolidine | F | 1-(3-amino)pyrrolidinyl | cyclopropyl |
| N-methoxyamine | 3-dimethylaminopyrrolidine | F | 1-(3-dimethylamino)pyrrolidinyl | methoxy |
| ethylamine | 3-dimethylaminopyrrolidine | F | 1-(3-dimethylamino)pyrrolidinyl | ethyl |
| cyclopropylamine | 3-dimethylaminopyrrolidine | F | 1-(3-dimethylamino)pyrrolidinyl | cyclopropyl |
| ethylamine | sodium cyanide | F | cyano | ethyl |
| ethylamine | methylthiol | F | methylmercapto | ethyl |
| cyclopropylamine | 1,2-diaminoethane | F | 2-aminoethylamino | cyclopropyl |
| cyclopropylamine | 2-dimethylaminoethyl-amine | F | 2-dimethylamino-ethylamino | cyclopropyl |
| ethylamine | 2-dimethylaminoethylamine | F | 2-dimethylamino-ethylamino | ethyl |

In addition, by following the procedure of Example 1, but replacing the 2,4-dichloro-5-fluoroacetophenone starting material and aniline in Example 1 with the compounds set forth in Table II, the following compounds of formula I wherein $R_2$ is hydrogen, and their hydrochloride salts, are obtained.

TABLE II

| 2,4-Dichloro-5-fluoro acetophenone Replacement | Aniline Replacement | Compound Obtained $R_0$ | R | $R_1$ |
|---|---|---|---|---|
| 2-chloro-5-fluoro-acetophene | ethylamine | F | H | ethyl |
| 2-chloro-4-methyl-5-fluoro-acetophenone | cyclopropylamine | F | $CH_3$ | cyclopropyl |
| 2-chloro-4-(4-pyridyl)-5-fluoroacetophenone | ethylamine | F | 4-pyridyl | ethyl |
| 2-chloro-4-(4-pyridyl)-acetophenone | ethylamine | H | 4-pyridyl | ethyl |
| 2-chloro-4-(4-pyridyl)-acetophenone | cyclopropylamine | H | 4-pyridyl | cyclopropyl |
| 2-chloro-4-(4-pyridyl)-5-fluoroacetophenone | cyclopropylamine | F | 4-pyridyl | cyclopropyl |
| 2-chloro-4,5-difluoro-acetophenone | ethylamine | F | F | ethyl |
| 2-chloro-4,5-difluoro acetophenone | cyclopropylamine | F | F | cyclopropyl |
| 2-chloro-4-chloromethyl-5-fluoroacetophenone | ethylamine | F | $CH_2Cl$ | ethyl |
| 2-chloro-4-methoxy-5-fluoroacetophenone | ethylamine | F | methoxy | ethyl |
| 2-chloro-4-nitro-5-fluoroacetophenone | cyclopropylamine | F | nitro | cyclopropyl |
| 2-chloro-4-phenyl-5-fluoroacetophenone | ethylamine | F | phenyl | ethyl |
| 2-chloro-4,5-methylene-dioxy-acetophenone | ethylamine | $R_0 + R = O-CH_2O$ | | ethyl |
| 2-chloro-4,5-methylene-dioxy-acetophenone | cyclopropylamine | $R_0 + R = O-CH_2O$ | | cyclopropyl |
| 5-chloro-6-acetylindene | ethylamine | $R_0 + R = CH_2CH=CH$ | | ethyl |
| 2,3-dihydro-5-acetyl-6-chlorobenzofuran | cyclopropylamine | $R_0 + R = CH_2CH_2O$ | | cyclopropyl |
| 2,3-dihydro-5-chloro-6-acetylbenzofuran | ethylamine | $R_0 + R = O-CH_2CH_2$ | | ethyl |
| 5-chloro-6-acetylbenzofuran | ethylamine | $R_0 + R = O-CH=CH$ | | ethyl |
| 5-acetyl-6-chlorobenzofuran | cyclopropylamine | $R_0 + R = CH=CH-O$ | | cyclopropyl |
| 5-acetyl-6-chloroindene | ethylamine | $R_0 + R = CH=CH-CH_2$ | | ethyl |

What is claimed is:

1. A compound of the formula:

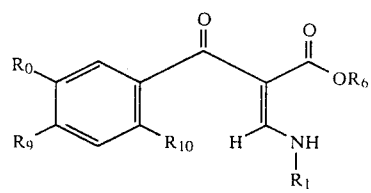

wherein $R_0$ is halo; $R_1$ is substituted phenyl of the formula

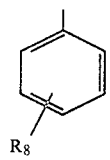

wherein $R_8$ represents one or two halo atoms substituted on the phenyl ring; $R_6$ is alkyl of 1 to 10 carbon atoms, phenyl or benzyl; $R_9$ is halogen; and $R_{10}$ is a leaving group selected from halo, alkoxy, -S-alkyl, -O-tosyl and -O-mesyl.

2. A compound of claim 1 wherein $R_9$ is fluoro or chloro and $R_{10}$ is a leaving group selected from halo, alkoxy, -S-alkyl, -O-tosyl and -O-mesyl.

3. A compound of claim 2 wherein $R_6$ is loweralkyl.
4. A compound of claim 2 wherein $R_0$ is fluoro.
5. A compound of claim 1 wherein $R_0$ is fluoro and $R_9$ and $R_{10}$ are chloro.
6. A compound of claim 5 wherein $R_6$ is ethyl.

7. The compound of claim 1 having the formula:

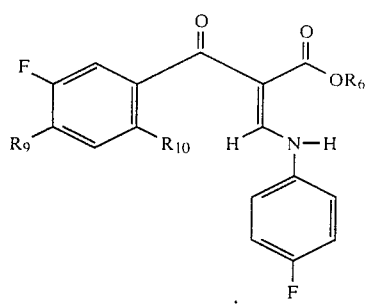

wherein $R_9$ and $R_{10}$ are independently selected from chloro and fluoro and $R_6$ is methyl or ethyl.

8. The compound of claim 1 having the formula:

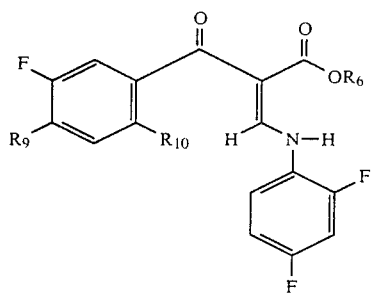

wherein $R_9$ and $R_{10}$ are independently selected from chloro and fluoro and $R_6$ is methyl or ethyl.